(12) United States Patent
Slater et al.

(10) Patent No.: US 6,225,630 B1
(45) Date of Patent: *May 1, 2001

(54) APPARATUS CONFIGURED FOR IDENTIFICATION OF A MATERIAL AND METHOD OF IDENTIFYING A MATERIAL

(75) Inventors: John M. Slater; Thomas M. Crawford; Dean A. Frickey, all of Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/205,265

(22) Filed: Dec. 3, 1998

(51) Int. Cl.$^7$ ................................................ G01N 21/61
(52) U.S. Cl. .................. 250/343; 250/339.13; 250/351
(58) Field of Search .............................. 250/343, 339.13, 250/351

(56) References Cited

U.S. PATENT DOCUMENTS

| | | | |
|---|---|---|---|
| 4,201,468 | 5/1980 | Margolis et al. | |
| 4,733,397 | * 3/1988 | Gallagher et al. | 372/26 |
| 6,069,702 | * 5/2000 | Slater et al. | 356/388 |

OTHER PUBLICATIONS

*Progress With Optical Gas Sensors Using Correlation Spectroscopy*, J.P. Dakin, H.O. Edwards, B.H. Weigl, Elsevier Science S.A., 1995, pp. 87–93.
*A New Concept for Open–Path Air Pollution Monitoring*, L.H. Taylor, Sensors, Apr. 1995.
*Gas Sensors Using Correlation Spectroscopy Compatible With Fibre–Optic Operation*, H.O. Edwards and J.P. Dakin, Optoelectronics Research Center, 1993, Sensors and Actuators 13, 11 (1993) pp. 9–19.
*Near–Infrared Diode Lasers Monitor Molecular Species*, David E. Cooper and Ramon U. Martinelli, Laser Focus World, Nov. 1992, 4 pages.
*Optical Remote Measurement of Toxic Gases*, William B. Grant, Robert H. Kagann and William A. McClenny, Air & Waste Management Association, Jan. 1992, pp. 18–31.
*Non–Mechanical Optical Path Switching and Its Application to Dual Beam Spectroscopy Including Gas Filter Correlation Radiometry*, Glen W. Sachse and Liang–Guo Wang, NASA Case No. LAR 14588–1–CU, Feb. 11, 1991, 19 pages.
*IR Long–Path Photometry: A Remote Sensing Tool for Automobile Emissions*, Gary A. Bishop, John R. Starkey, Anne Ihlenfeldt, Walter J. Williams, and Donald H. Stedman, Analytical Chemistry, vol. 61, No. 10, May 15, 1989, 6 pages.
*Detection of Organic Vapors With Active and Passive Sensors: A Comparison*, Dennis F. Flanigan, Applied Optics, vol. 25, No. 23, Dec. 1986, pp. 4253–4260.

(List continued on next page.)

*Primary Examiner*—Seungsook Ham
*Assistant Examiner*—Richard Hanig
(74) *Attorney, Agent, or Firm*—Wells St John Roberts Gregory & Matkin

(57) ABSTRACT

The present invention relates to an apparatus configured for identification of a material and method of identifying a material. One embodiment of the present invention provides an apparatus configured for identification of a material including a first region configured to receive a first sample and output a first spectrum responsive to exposure of the first sample to radiation; a signal generator configured to provide a reference signal having a reference frequency and a modulation signal having a modulation frequency; a modulator configured to selectively modulate the first spectrum using the modulation signal according to the reference frequency; a second region configured to receive a second sample and output a second spectrum responsive to exposure of the second sample to the first spectrum; and a detector configured to detect the second spectrum.

60 Claims, 3 Drawing Sheets

OTHER PUBLICATIONS

*Electrooptic Phase Modulation Gas Correlation Spectroscopy: a Laboratory Demonstration*, David M. Rider, J.T. Schofield, J.S. Margolis, and D.J. McCleese, Applied Optics, vol. 25, No. 17, Sep. 1986, pp. 2860–2862.

*Spectral Signatures of Chemical Agents and Simulants*, Lynn D. Hoffland, Ronald J. Piffath, James B. Bouck, Optical Engineering, vol. 24, No. 6, Nov./Dec. 1985, 3 pages.

*Gas Concentration Measurement by Spectral Correlation: Rejection of Interferent Species*, Andre Galais, Gerard Fortunato, and Pierre Chavel, Applied Optics, vol. 24, No. 14, Jul. 15, 1985, pp. 2127–2135.

*Remote Sensing of Stratospheric and Mesospheric Winds by Gas Correlation Electrooptic Phase–Modulation Spectroscopy*, Daniel J. McCleese and Jack S. Margolis, Applied Optics, vol. 22, No. 27, Sep. 1983, pp. 2528–2534.

*Carbon Monoxide Mixing Ratio Inference From Gas Filter Radiometer Data*, H. Andrew Wallio, Joseph C. Casas, Barbara B. Gormsen, Henry G. Reichle, Jr., and Mary S. Saylor, Applied Optics, vol. 22, No. 5, Mar. 1, 1983, pp. 749–755.

*Electro–Optic Modulation Applied to Correlation Spectroscopy*, Jack S. Margolis and Daniel J. McCleese, Jet Propulsion Laboratory, Jan. 10–13, 1983, 4 pages.

*Gas Cell Correlation Spectrometer: GASPEC*, T.V. Ward and H.H. Zwick, Applied Optics, vol. 14, No. 12, May 19, 1975, pp. 2896–2904.

*Remote Detection of Gases by Gas Correlation Spectroradiometry*, J.S. Margolis, D.J. McCleese, and J.V. Martonchik, Jet propulsion Laboratory, pp. 114–117.

*Remote Sensing of Upper Atmosphere Winds*, D.J. McCleese and J.S. Margolis, Jet Propulsion Laboratory, 4 pages.

\* cited by examiner

APPARATUS CONFIGURED FOR IDENTIFICATION OF A MATERIAL AND METHOD OF IDENTIFYING A MATERIAL

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

TECHNICAL FIELD

The present invention relates to an apparatus configured for identification of a material and a method of identifying a material.

BACKGROUND OF THE INVENTION

Detection devices for identifying chemical species and other materials are known in the art. Spectroscopy has been utilized in detection and identification applications. Conventional material or chemical detection technologies can be classified into general categories.

A first category includes lidar techniques which reflect or scatter a laser beam from a scene. The laser beam is tuned across a spectroscopic absorption feature of the target gas and differential absorption of returning photons is used for target detection. Because of the complex laser technology utilized to provide appropriate power (e.g., optical parametric generators), these systems are typically built to sense only one or a few compounds. The use of a laser beam precludes use of these techniques in covert applications. A recent development in this technology is the availability of simple laser diodes, however these diodes are minimally tunable and therefore are essentially built to detect single compounds.

Another category comprises open-path FTIR (Fourier transform infrared) spectrometers. Such spectrometers often use a broadband light source in combination with a Fourier transform spectrometer. The light sources employed are typically weak and require a high reflectance mirror. These systems have not yet achieved a desirable level of robustness or sensitivity achievable with lidar systems.

Other spectrometry techniques utilize passive infrared. These infrared systems typically use a spectrometer and highly sensitive detector to examine passively occurring emission or absorption lines. This technique has the benefits of being inherently covert and capable of sensitivities comparable to active techniques.

Techniques employing conventional spectrometry typically use dispersive, refractive, or interference-filter based optics. Such spectrometers have the disadvantage of requiring careful calibration to certain wavelength regions in order to admit only the spectral line of interest.

Another detection method includes reference cell spectroscopy or gas filter correlation (GFC) spectroscopy. Conventional reference cell spectroscopy utilizes a reference gas cell on a rotating platform which can be configured to alternately block and unblock incoming light to produce modulation in the input and output of a downstream detector. Alternatively, an alternating/rotating beamsplitter can be utilized.

The basic concept is that the degree of modulation due to insertion of a reference cell depends upon whether or not the input spectrum has spectral features that correlate with those of the absorption cell. This conventional technique is severely limited by a host of instrumental problems including those resulting from the use of multiple optical paths.

In this technique, incoming light containing spectral information is alternatingly transmitted over separate optical paths. One path contains a cell having a gas to be analyzed and the other path serves as a control. A light switch or mechanical method is utilized to change from one path to the other. The light intensity of the two paths is compared.

Problems exist with the utilization of this conventional technique. The technique is subject to leg imbalance due to various drift effects. A lack of balance between the signal and reference optical paths makes it difficult to determine whether a detected "signal" is actually due to the spectral lines of interest or the lack of proper calibration or balance of the instrument. In addition, the intensity balance of two-leg systems which can be maintained over a substantial period of time is about 0.5 percent of the optical intensity in either leg. Thus, detected absorption over substantial time periods is limited to approximately this level.

Therefore, there exists a need to provide improved apparatuses and methods for detecting materials, such as, for example, chemical compounds, which avoid the problems associated with the prior art.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
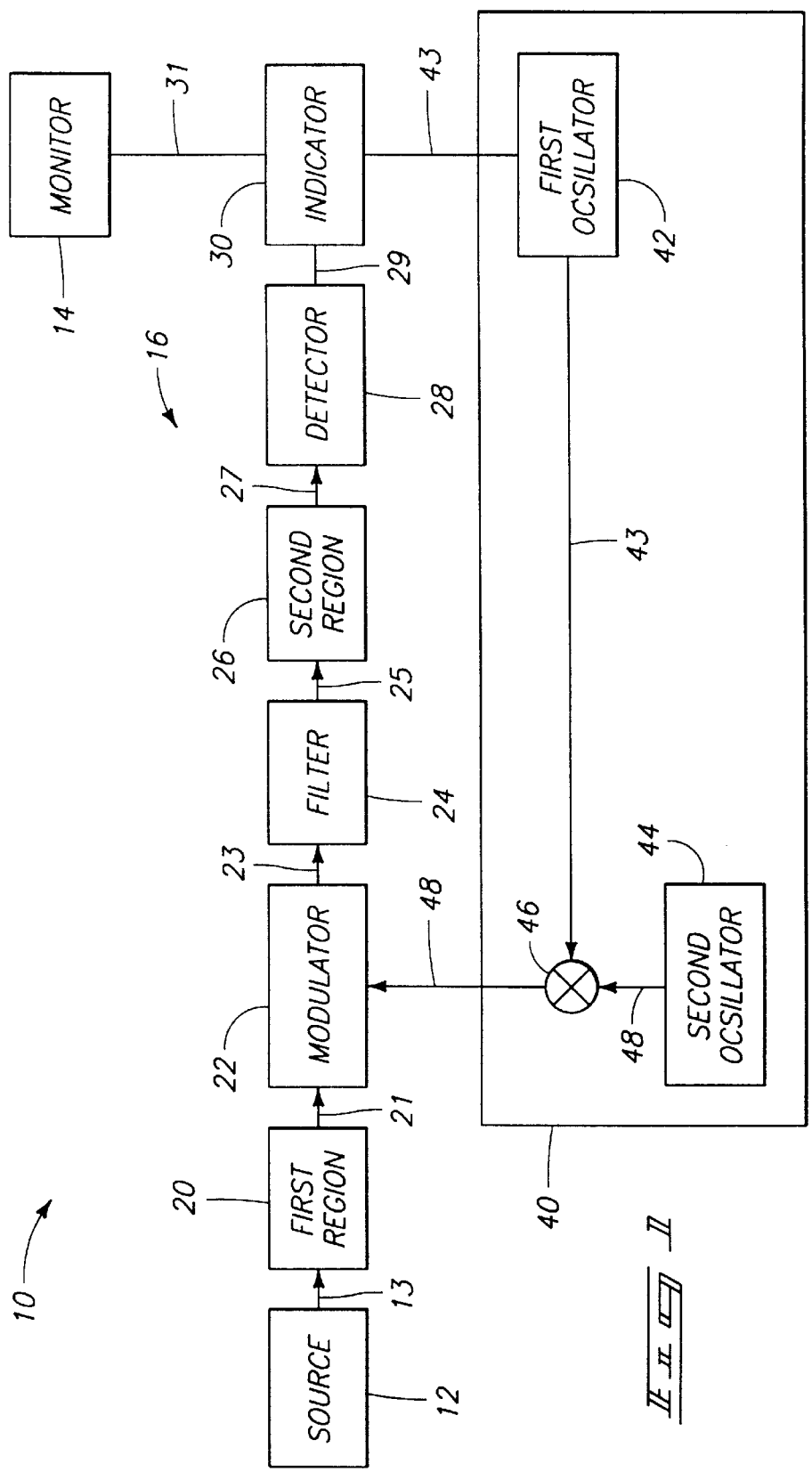
FIG. 1 is a functional block diagram of one embodiment of an apparatus configured for identification of a material.

This disclosure of the invention is submitted in furtherance of the constitutional purposes of the U.S. Patent Laws "to promote the progress of science and useful arts" (Article 1, Section 8).

Light passing through a material, such as a chemical species, present in a sample will have certain characteristic wavelengths absorbed or emitted. Radiation or light is preferably passed through two samples provided within plural regions. According to one embodiment, one sample includes a reference or known material and the other sample includes a material to be characterized or detected. For example, one region can comprise a plume of atmospheric air from a monitored environment. The other region can contain a reference material or chemical. The apparatuses and methods of the present invention are configured to identify materials present in the reference region within the plume.

The present invention is configured to provide indication of materials having spectra over a wide range of frequencies. Preferably, the present invention is configured to detect chemicals having spectra in the infrared, visible, and ultraviolet wavelength regions. In addition, apparatuses and methods disclosed herein can be embodied as a passive system.

The apparatuses and methods of the invention utilize modulation of a spectrum of a material to provide detection.

The apparatuses and methods utilize the material to be identified as a filter to detect the presence of the same material in the atmosphere or other sample. The present invention performs high resolution spectroscopy without alignment or registration requirements in a preferred embodiment. The invention is preferably configured to sense minute amounts of a material or chemical species in the sample or atmosphere.

Embodiments disclosed herein can be configured to wavelength modulate an incoming spectra or light beam by an amount on the order of an absorption or emission bandwidth of typical narrow band materials or chemicals species. Preferred apparatuses and methods are configured to provide frequency modulation of a gigahertz or higher. Such enables sensitivity to the presence of narrow lined (e.g., less than 10 GHz linewidth) materials or chemical species present in a sample, such as at atmospheric pressure. Molecules with narrow line spectra will tend to be those having a moderately low atomic number when viewed at atmospheric or lower pressures. The C–H stretch in the 3–4 micron region and overtones in the 1.5 micron region are examples.

According to one embodiment of the present invention, an apparatus configured for identification of a material comprises: a first region configured to receive a first sample and output a first spectrum responsive to exposure of the first sample to radiation; a signal generator configured to provide a reference signal having a reference frequency and a modulation signal having a modulation frequency; a modulator configured to selectively modulate the first spectrum using the modulation signal according to the reference frequency; a second region configured to receive a second sample and output a second spectrum responsive to exposure of the second sample to the first spectrum; and a detector configured to detect the second spectrum.

A second embodiment of the present invention provides an apparatus configured for identification of a material within a sample comprising: a source configured to emit radiation; a first region optically coupled in series with the source and configured to receive a first sample, the first region being configured to output a first spectrum responsive to exposure of the first sample to the radiation; an optical modulator optically coupled in series with the first region and configured to modulate the first spectrum; a first oscillator configured to generate a microwave modulation signal; a second oscillator configured to generate a reference signal having a frequency less than the modulation signal; a switch coupled with the optical modulator and the first oscillator and the second oscillator, the switch being configured to selectively apply the modulation signal to the modulator responsive to the reference signal; a second region optically coupled in series with the optical modulator and configured to receive a second sample and output a second spectrum responsive to exposure of the second sample to the first spectrum; a detector optically coupled in series with the second region and configured to receive the second spectrum and output a detection signal at the frequency of the reference signal responsive to a material being present in the first sample and second sample; and an indicator configured to compare the detection signal and the reference signal, the indicator being further configured to indicate the presence of the material within the first region and second region.

Another embodiment of the present invention provides a method of identifying a material comprising: providing a source; providing a first sample and a second sample; first exposing the first sample to the source and forming a first spectrum; periodically modulating the first spectrum at a modulation frequency according to a reference frequency; second exposing the second sample to the modulated first spectrum and forming a second spectrum; and detecting the second spectrum.

According to another embodiment, the invention provides a method of identifying a material comprising: providing a first sample and a second sample; forming a first spectrum using the first sample; generating a modulation signal having a modulation frequency; selectively applying the modulation signal to a modulator according to a reference frequency; modulating the first spectrum using the modulator responsive to the modulation signal; exposing the second sample to the modulated first spectrum and forming a second spectrum; and detecting the second spectrum at the reference frequency.

Yet another embodiment of the invention provides a method of identifying a material comprising: forming a first spectrum using a first sample; selectively modulating the first spectrum using a modulation signal according to a reference frequency; forming a second spectrum using a second sample, the second spectrum being amplitude modulated corresponding to the reference frequency; comparing a frequency of modulation of the second spectrum with the reference frequency; and indicating the presence of a material within the first sample and the second sample responsive to the comparing.

Referring to FIG. 1, an apparatus 10 configured for identifying a material is illustrated. An exemplary material includes a chemical species. The chemical species preferably has a narrow spectral features with linewidth of less than approximately 10 GHz vibrational spectra, or overtone spectra in the 0.1–10 micron range. Apparatus 10 according to the present invention provides spectroscopic analysis by comparing spectra of samples which may have a common material or chemical species. Apparatus 10 can be configured to detect a material via electronic, vibrational and rotational spectral features.

Apparatus 10 is generally insensitive to interference from other species. Further, the described embodiment provides a single optical path correlation technique which is substantially insensitive to optical misalignments. Apparatus 10 is configured in a preferred embodiment to provide detection of materials located within the atmosphere at ambient or atmospheric pressures or lower. Apparatus 10 can be utilized for detection or process control in exemplary applications.

The illustrated apparatus 10 comprises a source 12, first region 20, modulator 22, filter 24, second region 26, detector 28, indicator 30 and signal generator 40. In a preferred arrangement, source 12, regions 20, 26, modulator 22, filter 24 and detector 28 are optically coupled in series and define a single optical path 16.

Source 12 is configured to emit radiation 13. An exemplary source 12 includes a broadband light source. Emitted radiation 13 passing through optical path 16 of apparatus 10 is represented by arrows in FIG. 1.

First region 20 and second region 26 are optically coupled with source 12 and configured to receive radiation 13. First region 20 and second region 26 are individually configured to receive a first sample and a second sample, respectively. The first sample and the second sample individually comprise one of a reference material, and a material to be characterized. Some of radiation 13 can be absorbed by the first and second samples. Alternatively, exposed samples can emit respective spectra responsive to exposure to radiation 13.

In one embodiment, the individual one of regions 20, 26 having the reference material comprises a cell. Provision of the reference material within a cell minimizes exposure of the reference to external contamination. Additionally, the other one of regions 20, 26 can receive a plume of atmospheric air, or other media containing the material to be characterized. In monitoring applications it is preferred to provide access or otherwise expose the individual region 20, 26 having the material to be characterized to the surroundings.

First region 20 is configured to output a first spectrum 21 corresponding to the first sample and responsive to exposure of the first sample to radiation 13. Spectrum 21 can result from absorption of at least some of radiation 13. Alternatively, first spectrum 21 can be formed from emission responsive to exposure of the first sample to radiation 13.

Signal generator 40 is configured to provide a reference signal 43 having a reference frequency and a modulation signal 48 having a modulation frequency. In the described embodiment, reference signal 43 has a frequency less than modulation signal 48. Reference signal 43 has a frequency less than temporal bandwidths of detection devices described below in a preferred embodiment of the invention.

Signal generator 40 includes a first oscillator 42, second oscillator 44 and switch 46 in the depicted embodiment. The switch is equivalent to an electrical mixer. First oscillator 42 is configured to generate a reference signal 43 having a reference frequency. Reference signal 43 has a frequency in the range of 1 Hz–10 kHz in the described embodiment. A reference signal having other frequencies can be utilized.

Second oscillator 44 is configured to generate modulation signal 48. Second oscillator 44 is also referred to herein as an RF drive. Modulation signal 48 comprises a microwave signal in the preferred embodiment. Modulation signal 48 is within the range of 1–10 GHz in the described embodiment. In the present configuration, modulation signal 48 is 3 GHz or greater.

Switch 46 is coupled with optical modulator 22, first oscillator 42 and second oscillator 44 in the illustrated arrangement of signal generator 40. Switch 46 is configured to selectively apply modulation signal 48 to modulator 22 responsive to reference signal 43. Switch 46 modulates optical modulator 22 on and off according to reference signal 43.

Modulator 22 of apparatus 10 is optically coupled to first region 20 in the depicted embodiment. In a preferred embodiment, modulator 22 comprises an optical modulator. An exemplary optical modulator 22 comprises a crystal phase shifter having an index of refraction dependent upon an applied electric field.

Modulator 22 is configured to receive first spectrum 21 and modulation signal 48. Modulator 22 is preferably configured to selectively frequency modulate or wavelength shift first spectrum 21 using modulation signal 48. Modulator 22 is configured to selectively frequency modulate first spectrum 21 according to the reference frequency of reference signal 43. Varying the electric field applied via modulation signal 48 changes the index of refraction of modulator 22. Modulator 22 is preferably configured to provide a phase shift at peak voltage of approximately two waves or greater.

Modulator 22 outputs a periodically modulated first spectrum 23. First spectrum 21 is modulated by modulation signal 48 according to reference signal 43. Switch 46 selectively applies modulation signal 48 to modulator 22. Modulator 22 modulates first spectrum 21 at times when modulation signal 48 is passed via switch 46. Modulator 22 passes first spectrum 21 without modulation when modulation signal 48 is blocked via switch 46 or otherwise not applied to modulator 22.

Figure 2:
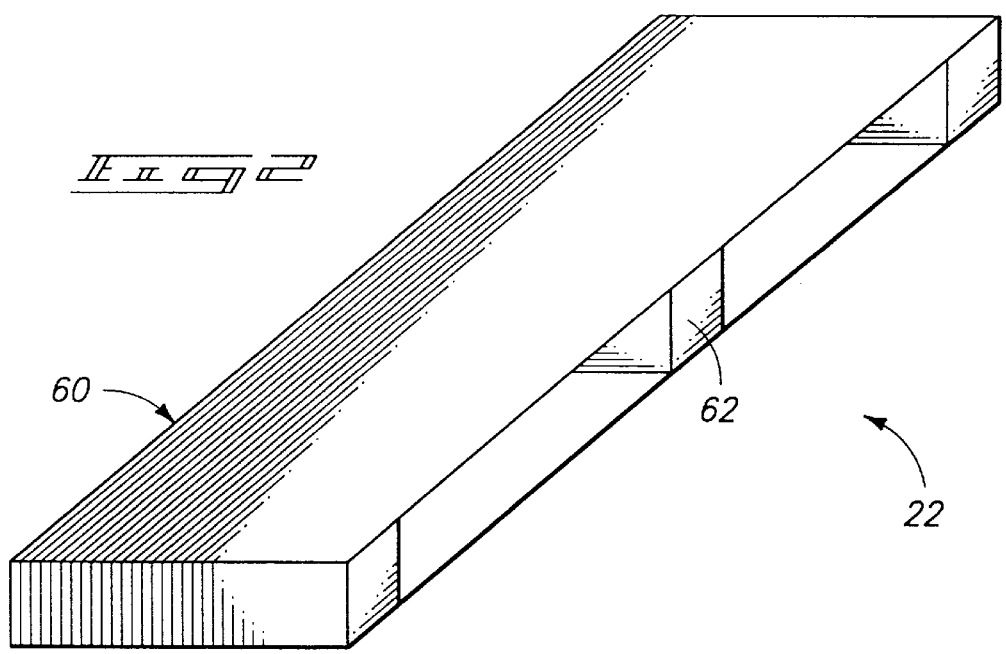
FIG. 2 is an isometric view of an embodiment of an optical modulator.

Referring to FIG. 2, one embodiment of modulator 22 is illustrated. The depicted modulator 22 comprises a wide field-of-view electro-optic phase modulator (EOPM). Modulator 22 includes a microstrip cavity 60 and a crystal 62 in one example. An exemplary crystal 62 comprises a lithium niobate crystal having a length (x axis) of 10 mm, a height (y axis) of 3 mm, and a width (z axis) of 3 mm. Modulator 22 preferably utilizes internal reflection within crystal 62 to increase the field of view. Other modulator 22 configurations and methods of periodically modulating first spectrum 21 can be utilized. For example, the Model 4433 Bulk E-0 modulator available from New Focus may be used.

Utilization of crystal 62 depicted in FIG. 2 provides a modulator 22 having a figure of merit which increases as the frequency shift increases and the optical throughput increases. Optical throughput is defined as the product of solid angle and beam area of the optical beam processed by modulator 22. The sensitivity of apparatus 10 increases as the figure of merit increases.

Figure 3:
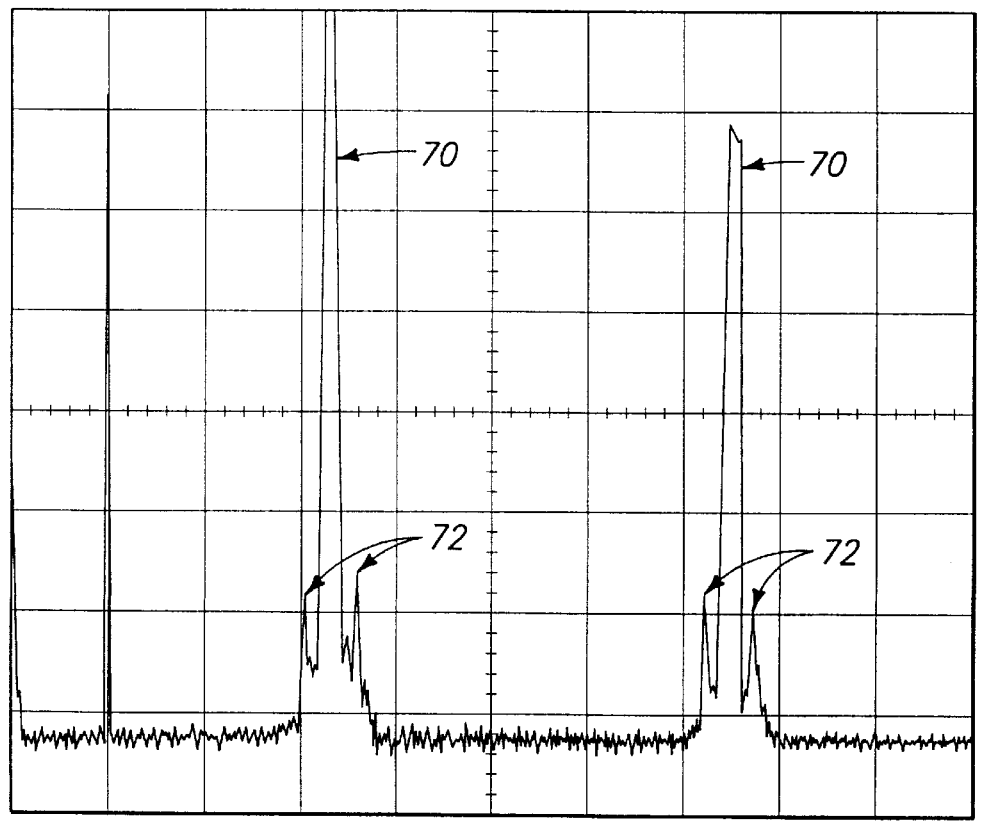
FIG. 3 is a graph illustrating modulation of a spectrum.

Referring to FIG. 3, an exemplary spectrum generated from the passage of light through an emissive or hot sample is illustrated. The depicted spectrum includes plural spectral lines 70. Phase shifting of incoming light or spectrum causes energy to fall in spectral sidebands 72 outside of the original spectral lines 70. The depicted sidebands 72 are shown shifted approximately +/−3 GHz from the center of spectral lines 70 responsive to 3 GHz modulation using modulator 22.

Sidebands 72 were generated in an experiment by passing a laser beam from a HeNe laser (6328 wavelength) through a lithium niobate crystal 62 of modulator 22 into a Fabry-Perot optical spectrum analyzer. The fundamental frequencies were present at lines 70 when microwave RF drive (second oscillator) 44 coupled with crystal 62 was turned off. With RF drive 44 on and adjusted between 50 and 100 watts, sidebands 72 appeared on the sides of the fundamental frequencies of the laser.

Modulator 22 preferably provides a sufficiently large frequency shift to move optical energy by an amount comparable to, or larger than, the linewidth of spectral lines 70. The frequency excursion produced by the Pockel's effects in an electro-optical modulator 22 is of the form:

$$\Delta f = kLmfE$$

where k is the wavenumber of the transmitted light, L is the length of crystal 62, m is the appropriate Pockel's coefficient for crystal 62, f is the RF frequency at which crystal 62 is driven (i.e., the frequency of modulation signal 48) and E is the applied electric field. This relationship applies for a single pass through a short crystal.

Filter 24 is configured to receive modulated first spectrum 23. Filter 24 preferably comprises an optical prefilter coupled downstream of modulator 22 in optical path 16. Filter 24 is configured to partially filter radiation emitted from source 12. In particular, filter 24 comprises a polarizer in one embodiment configured to remove unshifted photons from modulated first spectrum 23. Filter 24 can comprise a dielectric stack prefilter for reducing optical energy outside the spectral features of interest and therefore lowering the noise level within optical path 16. Filter 24 admits light centered on absorption or emission features of materials of interest aiding with the provision of an optical depth of second region 26 on the centers of spectral lines 70.

Filter 24 can be located at other positions within optical path 16 in other embodiments. Filter 24 outputs a filtered and modulated first spectrum 25. In an embodiment configured to detect water vapor within air, filter 24 was arranged as a 20 nm wide band pass filter centered at 1.6 microns.

Referring again to FIG. 1, second region 26 is optically coupled via optical path 16 with modulator 22 through filter 24. Second region 26 is configured to receive a second sample comprising either the reference material or the material to be characterized. Second region 26 is configured to output a second spectrum 27 corresponding to the second sample responsive to exposure of the second sample to filtered and periodically modulated first spectrum 25. In embodiments wherein filter 24 is not provided or is alternatively positioned at another location within optical path 16, second region 26 is configured to output second spectrum 27 responsive to exposure of the second sample to periodically modulated first spectrum 23.

Second spectrum 27 is formed from absorption of at least some of the periodically modulated first spectrum 25 in one embodiment. Alternatively, second spectrum 27 is formed from emission responsive to exposure of the second sample to first spectrum 25.

More specifically, second spectrum 27 comprises one of absorption or emission spectrum of the second sample. First spectrum 25 contains a periodically modulated absorption or emission spectrum of the first sample. First spectrum 25 is passed through second region 26 containing the second sample. Inasmuch as modulator 22 provides periodic frequency shifting of first spectrum 21, a periodic amplitude modulation of the light or radiation of second spectrum 27 results when the second sample is exposed to periodically modulated first spectrum 25 if a material is present within both samples. No modulation results with nonmatching materials within the first sample and the second sample inasmuch as there is no correlation of the respective spectra.

The optical energy absorbed in second region 26 is dependent upon the optical energy in sidebands 72. The optical output of second spectrum 27 decreases when modulation signal 48 (and the associated RF energy) is applied to modulator 22 in the case where the spectral lines are absorptive. Second spectrum 27 is amplitude modulated according to the frequency of reference signal 43 (i.e., responsive to modulation signal 48 being applied to modulator 22) when spectral correlation exists responsive to a material being present in the first sample and the second sample. The degree of spectral correlation between periodically modulated first spectrum 25 and that of the second sample determines the amplitude of the second spectrum 27.

Detector 28 is provided within optical path 16 and optically coupled with second region 26. Detector 28 is configured to receive second spectrum 27. In particular, detector 28 is configured to detect amplitude modulation of second spectrum 27 responsive to a material being present in the first and second samples. An exemplary detector 28 is model number HTE-2642 available from EG&G Optoelectronics Company.

In one embodiment, detector 28 is configured to detect or receive second spectrum 27 amplitude modulated according to the frequency of reference signal 43. Detector 28 is configured to output a detection signal 29 according to the frequency of amplitude modulation of second spectrum 27. Detector 28 is configured to output detection signal 29 at the frequency of reference signal 43 responsive to a material being present in the first sample of first region 20 and the second sample of second region 26.

Indicator 30 is coupled with detector 28 and signal generator 40. Indicator 30 is configured to receive reference signal 43 generated within oscillator 42. Further, indicator 30 is configured to receive detection signal 29 from detector 28. Indicator 30 is configured to indicate the presence of a common material within the first and second samples responsive to detection signal 29. Indicator 30 is configured to provide phase sensitive detection of detection signal 29 at the frequency of reference signal 43.

Indicator 30 is configured to compare reference signal 43 and detection signal 29. In particular, indicator 30 is configured to indicate the presence of a material responsive to second spectrum 27 being modulated at the frequency of reference signal 43 (i.e., frequency of modulation of detection signal 29 matches the reference frequency). Indicator 30 is configured to indicate the presence of a material within the first region 20 and second region 26 at ambient conditions (atmospheric pressure and temperature). In one embodiment, indicator 30 comprises a mixer or lock-in amplifier. An exemplary indicator 30 includes a Stanford Research Systems Model Number SR530.

In the depicted embodiment, a monitor 14 is coupled with indicator 30. Indicator 30 is configured to generate an indication signal 31 indicating the presence of a common material or chemical species within the respective first and second samples of first region 20 and second region 26. Monitor 14 can comprise a digital computer or other data gathering device in exemplary embodiments. Alternatively, monitor 14 can comprise an alarm if apparatus 10 is configured to detect harmful or toxic agents.

Figure 4:
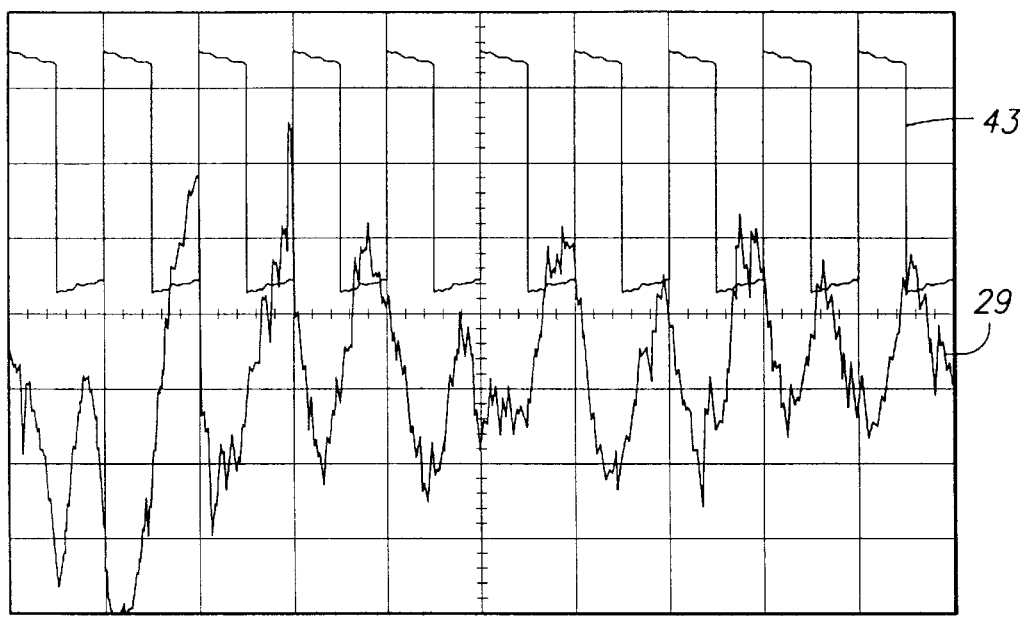
FIG. 4 is a graph illustrating a detection signal generated by an apparatus of the present invention responsive to a material being present.
Figure 5:
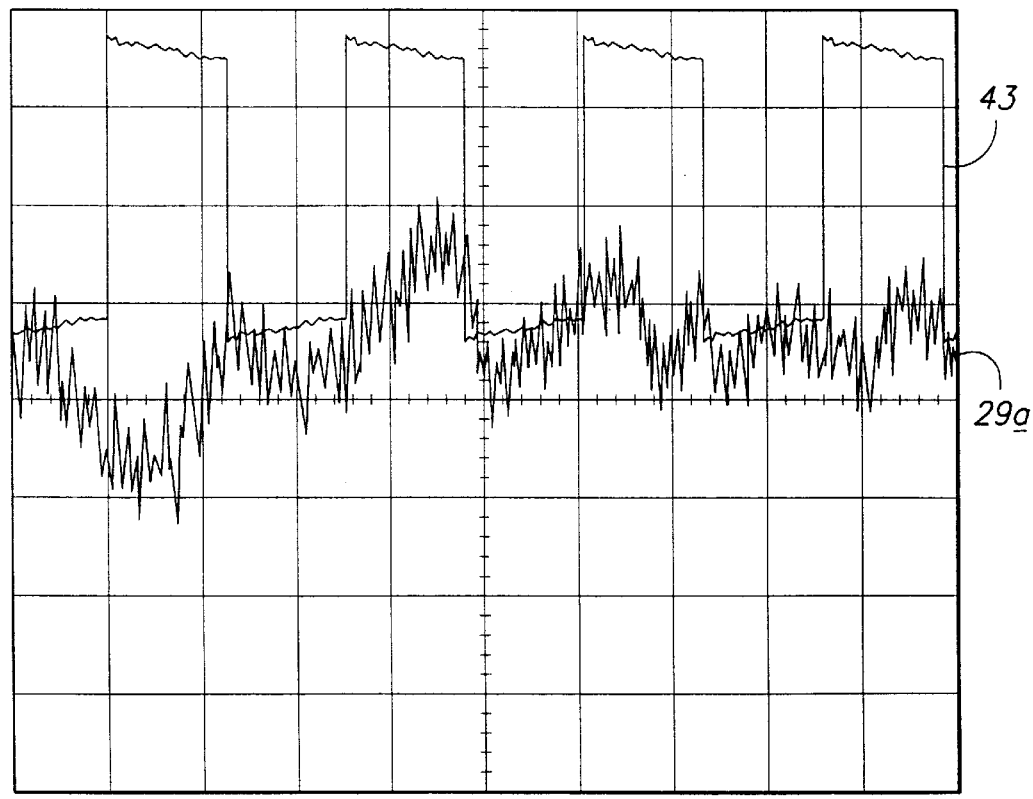
FIG. 5 is a graph illustrating a detection signal generated by an apparatus of the present invention responsive to a material not being present.

Referring to FIG. 4 and FIG. 5, exemplary plots are illustrated utilizing the Model 4433 Bulk E-0 modulator available from New Focus.

Referring to FIG. 4, detection signal 29 and reference signal 43 are shown in a plot where a common material is present in both the first sample and the second sample. Reference signal 43 is a 100 Hz square wave signal. Reference signal 43 controls the application of modulation signal 48 to modulator 22. Applying modulation signal 48 to modulator 22 or turning RF drive 44 on responsive to reference signal 43 being high results in detection signal 29 having low current as shown. Turning RF drive 44 off responsive to reference signal 43 being low results in detection signal 29 having high current. Such corresponds to the spectra of the first and second samples falling upon one another when first spectrum 21 is not modulated thereby passing more light through optical path 16 when a material is present in the first and second samples. Sidebands 72 block more light (e.g., during absorption spectrum) when modulation signal 48 is applied to modulator 22 causing the amount of detected light at detector 28 to decrease. As shown in FIG. 4, the frequency of detection signal 29 subsequently matches the frequency of reference signal 43.

Referring to FIG. 5, detection signal 29a and reference signal 43 are shown in a plot where no common material is present in both the first sample and the second sample. As shown in FIG. 4 and FIG. 5, the variation in current of detection signal 29a is less than the variation in current of detection signal 29. Indicator 30 is configured to distinguish between detection signal 29 corresponding to a material being present in both samples and detection signal 29a corresponding to no common material being present in the samples.

Utilizing a lock-in amplifier as the indicator, water vapor as the first and second samples, and a 100 Hz reference signal in one experiment, a three second integration time resulted in detection of a 1.9 mV of 100 Hz modulation detection signal with a DC signal of approximately 6 V from the broadband unmodulated light. The signal-to-noise ration was approximately sixty to one for the three second integration interval.

When water vapor was removed from one of the first and second samples, the voltage of the detection signal fell to 1.4 mV. The voltage of detection signal 29 then fell to 0.9 mV when water vapor was removed from the remaining sample. Replacement of either of the samples with a dry nitrogen cell (having no water vapor) illustrated that ambient water vapor accounted for the detected signal in the above illustration when one sample of water vapor was removed. Apparatus 10 configured in the illustrated arrangement is sensitive to ambient water vapor present in the atmosphere.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An apparatus configured for identification of a material, the apparatus comprising:
   a first region configured to receive a first sample and output a first spectrum responsive to exposure of the first sample to radiation;
   a signal generator configured to provide a reference signal having a reference frequency and a modulation signal having a microwave modulation frequency;
   a modulator configured to selectively modulate the first spectrum using the microwave modulation signal according to the reference frequency;
   a second region configured to receive a second sample and output a second spectrum responsive to exposure of the second sample to the first spectrum; and
   a detector configured to detect the second spectrum.

2. The apparatus according to claim 1 wherein the signal generator comprises:
   a first oscillator configured to generate the reference signal;
   a second oscillator configured to generate the modulation signal; and
   a switch configured to apply the modulation signal to the modulator responsive to the reference signal.

3. The apparatus according to claim 1 wherein the reference signal comprises a square wave.

4. The apparatus according to claim 1 wherein the second spectrum is modulated according to the reference signal and the detector is configured to output a detection signal at the reference frequency responsive to a material being present in the first sample and second sample.

5. The apparatus according to claim 1 wherein the second spectrum is modulated according to the reference signal and the detector is configured to output a detection signal according to the second spectrum.

6. The apparatus according to claim 5 further comprising an indicator configured to compare the reference signal and the detection signal and indicate the presence of a material.

7. The apparatus according to claim 1 further comprising an indicator coupled with the detector and configured to indicate the presence of a material.

8. The apparatus according to claim 7 wherein the indicator is configured to provide the indication at ambient conditions.

9. The apparatus according to claim 7 wherein the indicator comprises a lock-in amplifier.

10. The apparatus according to claim 1 wherein the modulation signal is a 3 GHz microwave signal.

11. The apparatus according to claim 1 wherein the first region, modulator, second region and detector are optically coupled in series.

12. The apparatus according to claim 1 wherein the modulator comprises an optical modulator.

13. The apparatus according to claim 1 further comprising a source optically coupled with the first region and configured to emit the radiation.

14. The apparatus according to claim 13 further comprising a filter optically coupled with the source and configured to partially filter the radiation.

15. The apparatus according to claim 13 wherein the first spectrum results from absorption of at least some of the radiation.

16. The apparatus according to claim 13 wherein the second spectrum results from absorption of at least some of the first spectrum.

17. The apparatus according to claim 13 wherein the first spectrum is formed from emission responsive to the radiation.

18. The apparatus according to claim 13 wherein the second spectrum is formed from emission responsive to the first spectrum.

19. The apparatus according to claim 1 wherein the first and second samples individually comprise one of a reference material and a material that is to be characterized.

20. The apparatus according to claim 19 wherein at least one of the first region and the second region comprise a cell configured to house the reference material.

21. An apparatus configured for identification of a material within a sample, the apparatus comprising:
   a source configured to emit radiation;
   a first region optically coupled in series with the source and configured to receive a first sample, the first region being configured to output a first spectrum responsive to exposure of the first sample to the radiation;
   an optical modulator optically coupled in series with the first region and configured to modulate the first spectrum;
   a first oscillator configured to generate a microwave modulation signal;
   a second oscillator configured to generate a reference signal having a frequency less than the modulation signal;
   a switch coupled with the optical modulator and the first oscillator and the second oscillator, the switch being configured to selectively apply the modulation signal to the modulator responsive to the reference signal;
   a second region optically coupled in series with the optical modulator and configured to receive a second sample and output a second spectrum responsive to exposure of the second sample to the first spectrum;
   a detector optically coupled in series with the second region and configured to receive the second spectrum and output a detection signal at the frequency of the reference signal responsive to a material being present in the first sample and second sample; and
   an indicator configured to compare the detection signal and the reference signal, the indicator being further configured to indicate the presence of the material within the first region and second region.

22. A method of identifying a material comprising:
   providing a source;
   providing a first sample and a second sample;
   first exposing the first sample to the source and forming a first spectrum;
   periodically modulating the first spectrum at a microwave modulation frequency according to a reference frequency;
   second exposing the second sample to the modulated first spectrum and forming a second spectrum; and detecting the second spectrum.

23. The method according to claim 22 further comprising generating a detection signal corresponding to modulation of the second spectrum at the reference frequency.

24. The method according to claim 22 further comprising indicating the presence of a material within the first sample and the second sample responsive to the detecting.

25. The method according to claim 22 further comprising indicating the presence of a material within the first sample and the second sample responsive to a modulation frequency of the second spectrum matching the reference frequency.

26. The method according to claim 22 wherein the modulating comprises periodically providing a modulation signal to a modulator according to the reference frequency.

27. The method according to claim 22 wherein the identifying the material comprises identifying at ambient conditions.

28. The method according to claim 22 wherein the modulating at a 3 GHz microwave frequency.

29. The method according to claim 22 wherein the modulating comprises modulating using an optical modulator.

30. The method according to claim 29 further comprising optically coupling the first sample, second sample and optical modulator in series.

31. The method according to claim 22 further comprising detecting amplitude modulation of the second spectrum at the reference frequency.

32. The method according to claim 31 wherein the providings of the first sample and the second sample individually comprise providing one of a reference material and a material that is to be characterized.

33. The method according to claim 31 further comprising emitting radiation from the source.

34. The method according to claim 33 further comprising filtering the radiation.

35. The method according to claim 33 wherein the forming the first spectrum comprises absorption of at least some of the emitted radiation.

36. The method according to claim 33 wherein the modulated first spectrum comprises radiation and the forming the second spectrum comprises absorption of at least some of the radiation of the modulated first spectrum.

37. The method according to claim 33 wherein the first sample emits the first spectrum responsive to exposure to the radiation.

38. The method according to claim 33 wherein the modulated first spectrum comprises radiation and the second sample emits the second spectrum responsive to exposure to the radiation of the modulated first spectrum.

39. A method of identifying a material comprising;
providing a first sample and a second sample;
forming a first spectrum using the first sample;
generating a modulation signal having a microwave modulation frequency;
selectively applying the modulation signal to a modulator according to a reference frequency;
modulating the first spectrum at a microwave frequency using the modulator responsive to the modulation signal;
exposing the second sample to the modulated first spectrum and forming a second spectrum; and
detecting the second spectrum at the reference frequency.

40. The method according to claim 39 further comprising generating a detection signal corresponding to modulation of the second spectrum at the reference frequency.

41. The method according to claim 39 further comprising indicating the presence of a material within the first sample and the second sample responsive to the detecting.

42. The method according to claim 39 further comprising indicating the presence of a material within the first sample and the second sample responsive to a frequency of modulation of the second spectrum matching the reference frequency.

43. The method according to claim 39 wherein the modulating comprises periodically providing a modulation signal to a modulator according to the reference frequency.

44. The method according to claim 39 wherein the identifying the material comprises identifying at ambient conditions.

45. The method according to claim 39 wherein the modulating comprises modulating at a 3 GHz microwave frequency.

46. The method according to claim 39 wherein the modulating comprises modulating using an optical modulator.

47. The method according to claim 46 further comprising optically coupling the first sample, second sample and optical modulator in series.

48. The method according to claim 39 further comprising detecting amplitude modulation of the second spectrum at the reference frequency.

49. The method according to claim 39 wherein the providings of the first sample and the second sample individually comprise providing one of a reference material and a material that is to be characterized.

50. A method of identifying a material comprising;
forming a first spectrum using a first sample;
selectively modulating the first spectrum using a microwave modulation signal according to a reference frequency;
forming a second spectrum using a second sample, the second spectrum being amplitude modulated corresponding to the reference frequency;
comparing a frequency of modulation of the second spectrum with the reference frequency; and
indicating the presence of a material within the first sample and the second sample responsive to the comparing.

51. The method according to claim 50 further comprising generating a detection signal corresponding to the second spectrum.

52. The method according to claim 51 wherein the comparing comprises comparing a frequency of the detection signal and the reference frequency.

53. The method according to claim 50 wherein the indicating is responsive to the frequency of modulation of the second spectrum matching the reference frequency.

54. The method according to claim 50 wherein the selectively modulating comprises periodically providing a modulation signal to a modulator according to the reference frequency.

55. The method according to claim 50 wherein the identifying the material comprises identifying at ambient conditions.

56. The method according to claim 50 wherein the modulating comprises modulating at a 3 GHz microwave frequency.

57. The method according to claim 50 wherein the modulating comprises modulating using an optical modulator.

58. The method according to claim 57 further comprising optically coupling the first sample, second sample and optical modulator in series.

59. The method according to claim 50 further comprising detecting the amplitude modulation of the second spectrum at the reference frequency.

60. The method according to claim 50 wherein the providings of the first sample and the second sample individually comprise providing one of a reference material and a material that is to be characterized.

* * * * *